United States Patent
Van Der Kouwe et al.

(10) Patent No.: US 10,459,058 B2
(45) Date of Patent: Oct. 29, 2019

(54) SYSTEM AND METHOD FOR MAGNETIC RESONANCE IMAGING WITH PROSPECTIVE MOTION CONTROL

(71) Applicant: THE GENERAL HOSPITAL CORPORATION, Boston, MA (US)

(72) Inventors: Andre J. W. Van Der Kouwe, Woburn, MA (US); Matthew D. Tisdall, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 282 days.

(21) Appl. No.: 15/301,860

(22) PCT Filed: Apr. 16, 2015

(86) PCT No.: PCT/US2015/026144
§ 371 (c)(1),
(2) Date: Oct. 4, 2016

(87) PCT Pub. No.: WO2015/161059
PCT Pub. Date: Oct. 22, 2015

(65) Prior Publication Data
US 2017/0219674 A1 Aug. 3, 2017

Related U.S. Application Data (60) Provisional application No. 61/981,452, filed on Apr. 18, 2014, provisional application No. 62/005,165, filed on May 30, 2014.

(51) Int. Cl.
*G01V 3/00* (2006.01)
*G01R 33/565* (2006.01)
(Continued)

(52) U.S. Cl.
CPC ........ *G01R 33/56509* (2013.01); *A61B 5/055* (2013.01); *G01R 33/483* (2013.01);
(Continued)

(58) Field of Classification Search
CPC ...................................................... A61B 5/055
(Continued)

(56) References Cited

U.S. PATENT DOCUMENTS 5,800,354 A * 9/1998 Hofland ........... G01R 33/56563
324/309
6,980,847 B2 * 12/2005 Peshkovsky ..... G01R 33/56509
324/308

(Continued)

OTHER PUBLICATIONS

International Search Report and Written Opinion dated Jul. 21, 2015 for International Application No. PCT/US2015/026144.
(Continued)

*Primary Examiner* — Louis M Arana
(74) *Attorney, Agent, or Firm* — Quarles & Brady LLP (57) ABSTRACT

A system and method for directing an MRI system to form echo signals from spins in a volume-of-interest (VOI) includes creating an integrated pulse sequence that integrates a volume navigator pulse sequence with an imaging pulse sequence by coordinating a navigator TR with an imaging TR to preserve a steady state of magnetization in the VOI associated with the imaging pulse sequence. The integrated pulse sequence includes performing the imaging pulse sequence to acquire imaging data from the VOI, performing the navigator pulse sequence to acquire navigator data VOI, processing the navigator data to generate motion estimates of motion in the VOI, creating an updated imaging pulse sequence that prospectively corrects for the motion in the VOI using the motion estimates, and repeating these steps using the updated imaging pulse sequence.

18 Claims, 4 Drawing Sheets

(51) Int. Cl.
*G01R 33/561* (2006.01)
*G01R 33/483* (2006.01)
*G01R 33/567* (2006.01)
*A61B 5/055* (2006.01)

(52) U.S. Cl.
CPC ..... *G01R 33/5613* (2013.01); *G01R 33/5616* (2013.01); *G01R 33/5673* (2013.01)

(58) Field of Classification Search
USPC .......................................... 324/306, 307, 309
See application file for complete search history.

(56) References Cited

U.S. PATENT DOCUMENTS

| | | | |
|---|---|---|---|
| 7,358,732 | B2 | 4/2008 | VAn Der Kouwe et al. |
| 9,696,401 | B2* | 7/2017 | Yui ................... G01R 33/5676 |
| 2003/0135105 | A1* | 7/2003 | Jack ................... G01R 33/5676 600/410 |
| 2007/0249929 | A1 | 10/2007 | Jeong et al. |
| 2010/0171497 | A1 | 7/2010 | Wadate et al. |
| 2013/0187649 | A1 | 7/2013 | Bhat et al. |

OTHER PUBLICATIONS

Alhamud et al. Volumetri navigators for real time motion correction in diffusion tensor imaging. Magn. Reson. Med. 68(4): 1097-1108, 2012 retrieved fro m the internet. retrieved on [Jun. 22, 2015] <URL: http//www.ncbi.nlm.nih.gov/pmc/articles/PMC3330197/pdf/nihms339050.pdf>.

* cited by examiner

SYSTEM AND METHOD FOR MAGNETIC RESONANCE IMAGING WITH PROSPECTIVE MOTION CONTROL

CROSS-REFERENCE TO RELATED APPLICATIONS

The application represents the U.S. National Stage of International Application No. PCT/US2015/026144, filed Apr. 16, 2015 which is based on, claims priority to, U.S. Provisional Application Ser. No. 61/981,452, filed Apr. 18, 2014, and U.S. Provisional Application Ser. No. 62/005,165, filed May 30, 2014, all of which are incorporated herein by reference for all purposes.

STATEMENT REGARDING FEDERALLY SPONSORED RESEARCH

This invention was made with government support under R01HD071664 awarded by the National Institutes of Health. The government has certain rights in the invention.

BACKGROUND

The field of the disclosure is systems and methods for magnetic resonance imaging ("MRI"). More particularly, the disclosure relates to systems and methods for tracking and controlling artifacts caused by motion during a MRI procedure.

MRI uses the nuclear magnetic resonance ("NMR") phenomenon to produce images. When a substance such as human tissue is subjected to a uniform magnetic field ("main magnetic field"), $B_0$, the individual magnetic moments of the nuclei in the tissue attempt to align with this magnetic field, but precess about it in random order at their characteristic Larmor frequency, $\omega$. If the substance, or tissue, is subjected to an excitation magnetic field, $B_1$, that is in the plane transverse to the main magnetic field, $B_0$, and that is near the Larmor frequency, $\omega$, the net aligned magnetic moment of the nuclei may be rotated, or "tipped," into the transverse plane to produce a net transverse magnetic moment. A signal is emitted by the excited nuclei, or "spins," after the excitation magnetic field, $B_1$, is terminated. The emitted signal may be received and processed to form an image.

When utilizing these emitted "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically-proven pulse sequences and they also enable the development of new pulse sequences.

Depending on the technique used, many MR scans currently require many minutes to acquire the necessary data used to produce medical images. The reduction of this scan time is an important consideration, since reduced scan time increases patient throughout, improves patient comfort, and improves image quality by reducing motion artifacts. Many different strategies have been developed to shorten the scan time.

For example, one popular category of pulse sequences are so-called gradient echo sequences. Within this category, the spoiled gradient echo and three-dimensional spoiled gradient-recalled echo (SPGR) or fast low angle shoot (FLASH) pulse sequences are often used in neuroimaging applications. Specifically, the SPGR or FLASH sequence forms the basis of many 3D neuroimaging sequences, but acquisition times often stretch to several minutes. Lengthy acquisitions in neuroimaging applications can be particularly troublesome because it is imperative that the subject remain motionless during the duration of the sequence. That is, in neuroimaging applications, motion can be particularly damaging to the resulting images because of the complexity of the structures being imaged and studied in neuroimaging applications.

Motion-correction systems in MRI can be grouped into two general methods: prospective and retrospective. Retrospective methods use information about the subject's motion to estimate what k-space data would have been measured if the subject had not moved during scanning. Prospective methods use motion-tracking data acquired during the scan to follow the subject with the gradient axes of the sequence, measuring the desired k-space data directly. Additionally, it is possible to combine the two methods so that retrospective processing corrects residual errors in the prospective system. A retrospective system can access all of the k-space data while performing reconstruction; a prospective system must necessarily rely only on previous measurements to estimate the current position of the patient. However, a prospective system avoids the need to estimate missing k-space data, allowing for direct reconstruction while avoiding possible sources of estimation error in the k-space data.

Also, one can differentiate between two types of motion correction problems that arise in MRI: between-scan motion and within-scan motion. For between-scan motion, several retrospective motion correction methods are available that register either slice-by-slice or volume-by-volume to estimate the data that would have been acquired in each volume if the subject had not moved. Prospective motion correction can also be employed for this problem, such as the orbital navigator system that inserts 3-plane circular k-space navigators, or the PACE system that registers each completed EPI volume back to the first time-point and so requires no navigators.

For in-scan motion, several methods are available, such as PROPELLER and the like that use redundant sampling of the center of k-space during each repetition time (TR) and estimate motion-free k-space data retrospectively. Also, prospective motion correction is available, such as by using cloverleaf navigators. The use of cloverleaf navigators is useful with SPGR/FLASH sequences.

However, in order to maximize SNR/time efficiency, short TR protocols are often used in neuroimaging applications. Such short-TR protocols, by definition, have very-little dead time and, thus, force navigators to be very short and provide limited k-space coverage. That is, as the TR is reduced, the effectiveness of the navigator is reduced because there is less information gathered by the navigator to use to form an estimate the subject's head motion.

It would therefore be desirable to provide a system and method for controlling the competing constraints of neuroimaging applications that desire extended acquisition times and the need to control or compensate or correct for patient motion during such acquisitions.

SUMMARY

The present disclosure overcomes the aforementioned drawbacks by providing a method for directing a magnetic resonance imaging (MRI) system to form echo signals from spins in a volume-of-interest (VOI). The method includes the steps of selecting an imaging pulse sequence that utilizes gradient fields to generate transverse magnetization to acquire imaging data from the VOI during an imaging repetition time (TR) and selecting a volume navigator pulse sequence that uses an echo-planar imaging (EPI) technique to acquire navigator data from the VOI during a navigator TR. The method also includes the step of creating an integrated pulse sequence that integrates the volume navigator pulse sequence with the imaging pulse sequence by coordinating the navigator TR with the imaging TR to preserve a steady state of magnetization in the VOI associated with the imaging pulse sequence. The method further includes performing, with the MRI system, the integrated pulse sequence by i) performing the imaging pulse sequence to acquire imaging data from the VOI, ii) performing the navigator pulse sequence to acquire navigator data VOI, and iii) process the navigator data to generate motion estimates of motion in the VOI. The method is also performed by iv) creating an updated imaging pulse sequence that prospectively corrects for the motion in the VOI using the motion estimates and v) repeating steps i) through iv) using the updated imaging pulse sequence. The method further includes reconstructing the imaging data to form at least one three-dimensional image of the VOI.

In accordance with another aspect of the disclosure, a magnetic resonance imaging (MRI) system is provided that includes a magnet system configured to generate a static magnetic field about at least a volume of interest (VOI) of a subject arranged in the MRI system and a gradient coil system configured to establish at least one magnetic gradient field with respect to the static magnetic field. The MRI system also includes a radio frequency (RF) system configured to deliver excitation pulses to the subject and acquire data from the subject and a computer system. The computer system is programmed to receive an indication of an imaging pulse sequence that utilizes gradient fields to generate transverse magnetization to acquire imaging data from the VOI during an imaging repetition time (TR) and receive an indication of a volume navigator pulse sequence that uses an echo-planar imaging (EPI) technique to acquire navigator data from the VOI during a navigator TR. The computer system is also programmed to create an integrated pulse sequence that integrates the volume navigator pulse sequence with the imaging pulse sequence by coordinating the navigator TR with the imaging TR to preserve a steady state of magnetization in the VOI associated with the imaging pulse sequence and control the gradient coil system and the RF system to perform the integrated pulse sequence. The integrated pulse sequence is performed by i) performing the imaging pulse sequence to acquire imaging data from the VOI, ii) performing the navigator pulse sequence to acquire navigator data VOI, and iii) processing the navigator data to generate motion estimates of motion in the VOI. The integrated pulse sequence is also performed by iv) creating an updated imaging pulse sequence that prospectively corrects for the motion in the VOI using the motion estimates, and v) repeating steps i) through iv) using the updated imaging pulse sequence. The computer system is further programmed to reconstruct the imaging data to form at least one three-dimensional image of the VOI.

In accordance with another aspect of the disclosure, a method is disclosed for directing a magnetic resonance imaging (MRI) system to form echo signals from spins in a volume-of-interest (VOI). The method includes a) selecting an imaging pulse sequence that utilizes gradient fields to generate transverse magnetization to acquire imaging data from the VOI during an imaging repetition time (TR) and b) selecting a volume navigator pulse sequence that uses an echo-planar imaging (EPI) technique to acquire navigator data from the VOI during a navigator TR. The method also includes c) creating an integrated pulse sequence that uses a common radio frequency (RF) pulse for the volume navigator pulse sequence and the imaging pulse sequence to preserve a steady state of magnetization in the VOI and d) performing, with the MRI system, the integrated pulse sequence. The integrated pulse sequence includes i) performing the imaging pulse sequence to acquire imaging data from the VOI, ii) performing the navigator pulse sequence to acquire navigator data VOI, and iii) processing the navigator data to generate motion estimates of motion in the VOI. The pulse sequence also includes iv) creating an updated imaging pulse sequence that prospectively corrects for the motion in the VOI using the motion estimates and v) repeating steps i) through iv) using the updated imaging pulse sequence. The method further includes e) reconstructing the imaging data to form at least one three-dimensional image of the VOI.

The foregoing and other aspects and advantages of the disclosure will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
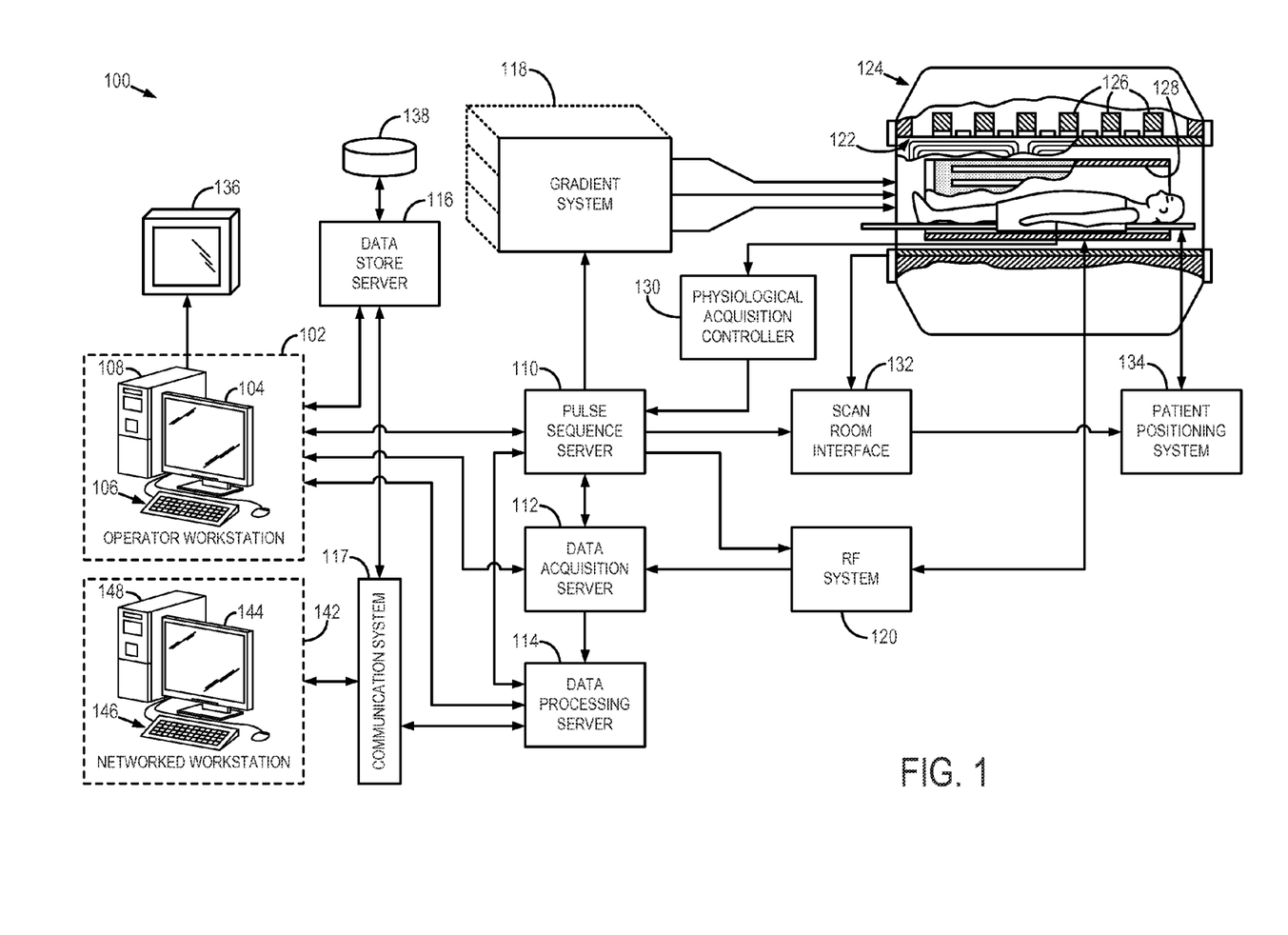
FIG. 1 is a block diagram of an example of a magnetic resonance imaging ("MRI") system.

Referring particularly now to FIG. 1, an example of a magnetic resonance imaging (MRI) system 100 is illustrated. The MRI system 100 includes an operator workstation 102, which will typically include a display 104, one or more input devices 106, such as a keyboard and mouse, and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 117, which may include any suitable network connection, whether wired, wireless, or a combination of both. As an example, the communication system 117 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients and used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil (not shown in FIG. 1), are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays (not shown in FIG. 1).

The RF system 120 also includes one or more RF receiver channels. Each RF receiver channel includes an RF preamplifier that amplifies the magnetic resonance signal received by the coil 128 to which it is connected, and a detector that detects and digitizes the quadrature components of the received magnetic resonance signal. The magnitude of the received magnetic resonance signal may, therefore, be determined at any sampled point by the square root of the sum of the squares of the and components:

$$M=\sqrt{I^2+Q^2}$$ Eqn. (1).

and the phase of the received magnetic resonance signal may also be determined according to the following relationship:

$$\varphi = \tan^{-1}\left(\frac{Q}{I}\right).$$ Eqn. (2)

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography (MRA) scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 117. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

As described, systems such as described above with respect to FIG. 1 have been used to perform neuroimaging acquisitions with short TRs, which force navigators to be very short provide limited k-space coverage. These navigators are often referred to as "ultra-fast navigators." The effectiveness of the navigators as a means through which to estimate the subject's head motion is limited.

In contrast to these ultra-fast navigators, echo-planar imaging (EPI)-based navigators or volume navigators (vNavs) have been used to acquire a whole-head volume in roughly 275 ms and, thereby, allow high-accuracy motion tracking. However, vNavs have previously only been used in sequences with significant dead time provided by inflow times (TI) or TR gaps in which the entire vNav could be inserted. However, as will be described, the present disclosure provides a way to insert a vNav into a 3D FLASH/SPGR sequence with only marginal impact on SNR or time. By doing so, the present disclosure provides a system and method for prospective motion correction of in-scan motion using a 3D FLASH/SPGR pulse sequence with vNavs that does not substantially extend acquisition times.

Figure 2:
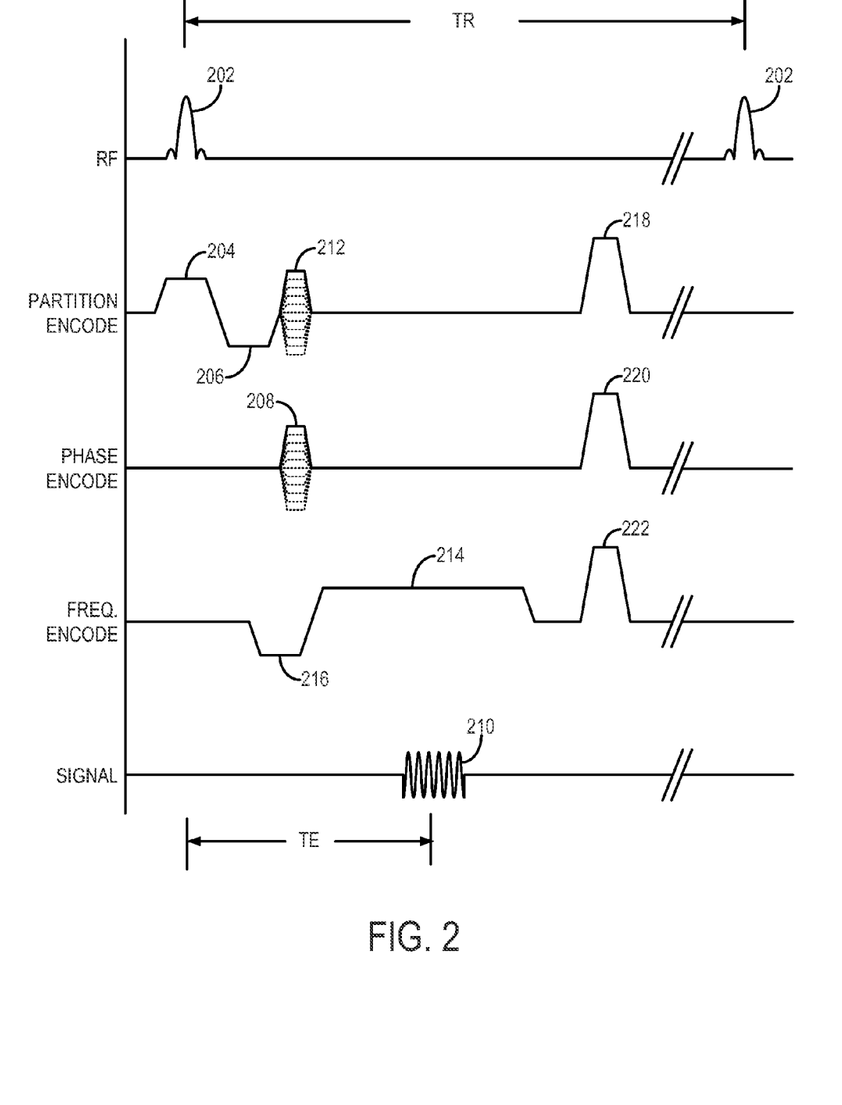
FIG. 2 is an example of a three-dimensional spoiled gradient-recalled echo ("3D SPGR") pulse sequence.

An example of a pulse sequence employed to direct an MRI system to acquire image data in accordance with some configurations of the present disclosure is illustrated in FIG. 2. The pulse sequence includes an RF excitation pulse 202 that is played out in the presence of a slab-selective gradient 204 in order to produce transverse magnetization in a volume-of-interest. The slab-selective gradient 204 includes a rephasing lobe 206 that acts to rephase unwanted phase dispersions introduced by the slab-selective gradient 204 such that signal losses resultant from these phase dispersions are mitigated.

Following excitation of the nuclear spins in the volume-of-interest, a phase-encoding gradient 208 is applied to spatially encode a nuclear magnetic resonance echo signal 210 at a given echo time (TE) representative of a gradient-recalled echo along one direction in the volume-of-interest. At the same time, a partition-encoding gradient 212 is applied to spatially encode the echo signal 210 along a second, orthogonal direction in the volume-of-interest. By way of example, the phase-encoding gradient 208 may spatially encode the echo signal 210 along the y-direction, while the partition-encoding gradient 212 may spatially encode the echo signal 210 along the z-direction. A readout gradient 214 is also applied after a dephasing gradient lobe 216 to spatially encode the echo signal 210 along a third, orthogonal direction in the volume-of-interest. By way of example, the readout gradient 214 may spatially encode the echo signal along the x-direction. The echo signal 210 is sampled during a data acquisition window.

Spoiler gradients 218, 220, 222 may be played out along the partition-encoding, phase-encoding, and frequency-encoding directions to dephase any residual transverse magnetization in the volume-of-interest to prevent signal contamination from one repetition time (TR) period to the next.

Figure 3:
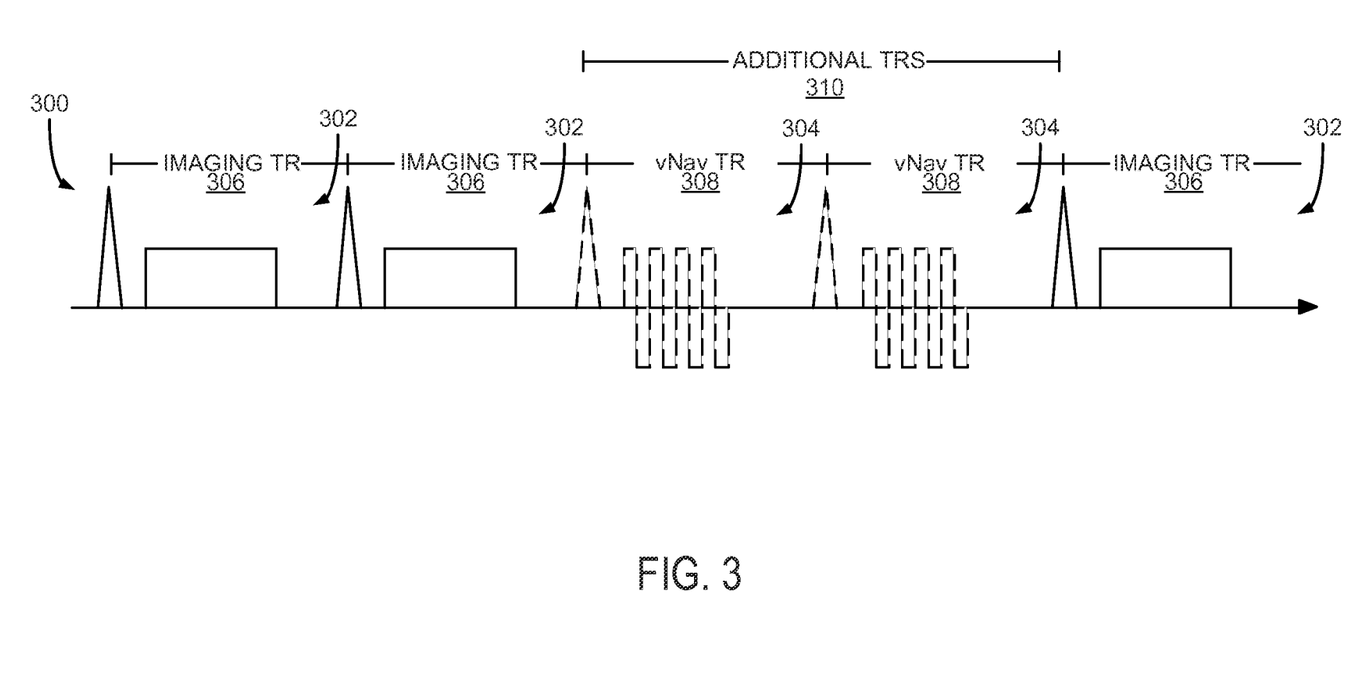
FIG. 3 is an example of a gradient-recalled echo ("GRE") pulse sequence that includes a self-refocusing slice-encoding gradient and self-refocusing phase-encoding gradient for differentially encoding image data acquired from multiple simultaneously excited slice locations.

Referring now to FIG. 3, the pulse sequence descried above with respect to FIG. 2 can, in accordance with the present disclosure, be combined with vNav sequences to yield a pulse sequence for performing prospective motion correction in SPGR/FLASH without extended TI or TR gaps. Specifically, FIG. 3 provides a timing diagram of an integrated vNav and a SPGR/FLASH sequence 300, showing common pulses and TRs, but varied gradients, for interleaved imaging and vNav sequences. In particular, a plurality of imaging sequences 302, such as described above with respect to FIG. 2 are illustrated. Integrated therewith are a plurality of vNav sequences 304. As will be described, the scan time of the 3D imaging sequence 302 is selected such that an imaging TR 306 allows a vNav TRs 308 to be inserted at any desired point. Furthermore, the RF pulses used in the vNav sequences 304 and the imaging sequences 302 may be the same. To this end, the steady-state of the imaging sequence 304 is maintained, even when vNav sequences 304 are inserted.

As an example, the vNav sequence 304 may be a 3D-encoded echo-planar imaging (EPI) pulse sequence with a 323 matrix and may be acquired with ¾ partial Fourier encoding in the partition direction. As such, in this example, the vNav sequence 304 may have 25 3D excitation pulses. In this example, assume a TR 308 for the vNav sequence 304 of 11 ms and assume that each 3D imaging sequence 302 has a TR 306 that matches the TR 308 of the vNav sequence 304. If the pulses of both sequences 302, 304 are matched, a train of 25 vNav TR (i.e., one vNav) can be played instead of a TR 306 of an imaging sequence 302 without disturbing the steady state of the imaging sequence 302. Expanding on this example, as long as the TR 306 of the imaging sequence 302 is 11 ms or longer, matching the vNav TR 308 to the imaging TR 308 can be readily achieved by adding TRs 310 to the vNav sequence 304 after its readouts and not simply attempting to fit the vNav TR 208 within dead time. Again, as long as the scan time of the 3D imaging sequence 302 meets the minimum TR requirement, vNav TRs 308 can be inserted at any desired point while maintaining the steady-state of the imaging sequence.

Inserting the vNav sequences 304 as separate TR 308 at any time allows a great deal of flexibility, but also increases overall scan time. In previous acquisitions using vNav sequences, the navigators were inserted in TR or TI gaps and, thus, did not increase scan time. However, continuing with the non-limiting example provided above 25 additional TRs are added to the total scan time with every vNav sequence while not gaining any additional imaging signal. To allow grater flexibility, as will be described, the user may set how many imaging TRs will be played between each vNav sequence, and the overall scan time is updated to inform users of the trade-off between tracking accuracy and scan time.

Figure 4:
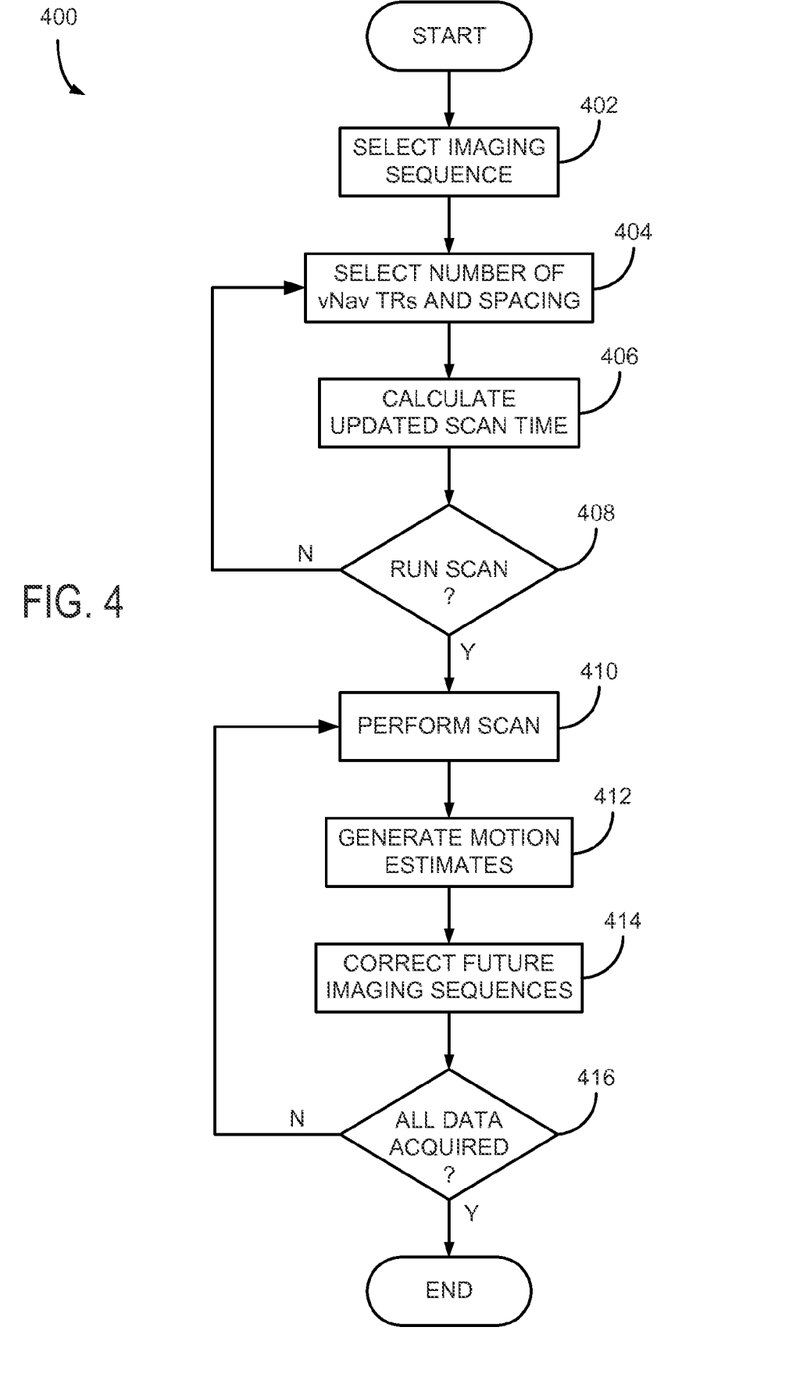
FIG. 4 is an example of an echo-planar imaging ("EPI") pulse sequence that includes a self-refocusing slice-encoding gradient, a self-refocusing phase-encoding gradients, and a series of successive slice-encoding gradient blips for differentially encoding image data acquired from multiple simultaneously excited slice locations.

Specifically, referring to FIG. 4, a flow chart is provided that sets forth an example of a process for performing prospective motion correction using the pulse sequence described with respect to FIG. 3. The prospective motion-corrected process 400 begins with user selection of the imaging pulse sequences and parameters for the sequence at process block 402. As described above, the imaging pulse sequence may be a FLASH or SPGR or other name for such gradient-echo sequences. Once the imaging sequence and parameters are selected, at process block 404, the user is prompted to select how many imaging TRs will be played between each vNav TR. Using this information, at process block 406, the overall scan time is updated to inform users of the trade-off between tracking accuracy and scan time. As indicated by decision block 408, the user may adjust the number and spacing of the vNav sequences to reach a desired overall scan time until the user has developed an overall integrated pulse sequence that is desired to be run.

At process block 410, scanning begins using the overall integrated pulse sequence built by the user as described above. Using the data acquired from each performance of the vNav pulse sequence, motion estimates are generated at process block 412. Specifically, the motion estimates are sent back to the scanner as they are generated on the image reconstruction computer, and are immediately applied at process block 414 to the coordinates of the next imaging sequence to provide real-time and prospective correction of subject motion that is identified. This process is repeated until, at decision block 416, all data has been acquired. This method is applicable both the three-dimensional acquisitions and to simultaneous multi-slice acquisitions, including when such acquisitions include in-place acceleration.

To test the efficacy of the above-described process, a human volunteer was scanned in a 3T TIM Trio (Siemens Healthcare, Erlangen, Germany) using a 32-channel head matrix. The imaging sequence was a FLASH pulse sequence that used a 15 degree flip angle, 11 ms TR, 3.43 ms TE, 200 Hz/px bandwidth, 256 mm×256 mm×176 mm FOV, and 1 mm isotropic resolution, and 2× GRAPPA acceleration for a total scan time of 4:48. One volume was acquired with this protocol while the subject remained still. Thereafter, a vNav sequence was inserted after every 136 FLASH TRs (approximately 1.5 seconds), increasing the scan time to 5:38, and acquired another volume while the subject remained still. Then, two more volumes were acquired with the vNavs sequences inserted, during both of which the subject was prompted to change their head position every minute, repeating the same motion pattern in both scans. In the first of these with-motion scans, correction was applied, using the following process, for the subject's motion in real time, while in the second with-motion scan not apply the update. FIG. 5 is a graph showing vNav-estimated head motion during a with-motion-correction scan. Translations are shown in x (blue), y (red), and z (yellow) and in mm, while rotation (green) is shown in degrees.

Thus, a system and method is provided for performing prospective motion correction in FLASH, SPGR, or FLASH/SPGR-like pulse sequences. Unlike previous navigator methods that attempted to insert ultra-fast navigators into the imaging (FLASH/SPGR) TR, the present disclosure provides a way to insert multiple matched vNav TRs into the overall pulse sequence train and, thus, preserves the steady state. The present disclosure recognizes that a navigator of substantial length, including vNavs, can be inserted or interleaved in a dense sequence imaging sequence (like FLASH), by substituting FLASH TRs for vNav TRs, while preserving the magnetization steady state. For example, to preserve the magnetization steady state, it is advantageous to match the vNav and FLASH TR times. Also, it is advantageous to ensure that the waveform of the excitation pulses match between the vNav and FLASH TRs. Further, if any gradients are used during the excitation pulse, it is advantageous to match these gradients. In addition, any RF spoiling between the vNav and FLASH TRs may be advantageously synchronized.

Unlike in previous applications of vNavs, where there was no scan-time increase, the additional TRs to accommodate the vNav sequence in the integrated FLASH-vNav pulse sequence does increase overall scan time. However, this drawback is overcome by the high registration accuracy enabled by whole-head navigators readily achieved with the vNav sequence. Furthermore, the additional scan time is still significantly less than what would be required for an MR technologist to request patient compliance and rescan. Additionally, the provided, integrated vNav-FLASH/SPGR sequence allows users the flexibility to trade-off scan time for tracking accuracy based on the needs of their application and the subject population involved.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for directing a magnetic resonance imaging (MRI) system to form echo signals from spins in a volume-of-interest (VOI), the steps of the method comprising:
   a) selecting an imaging pulse sequence that utilizes gradient fields to generate transverse magnetization to acquire imaging data from the VOI during an imaging repetition time (TR);
   b) selecting a volume navigator pulse sequence that uses an echo-planar imaging (EPI) technique to acquire navigator data from the VOI during a navigator TR;
   c) creating an integrated pulse sequence that integrates the volume navigator pulse sequence with the imaging pulse sequence by coordinating the navigator TR with the imaging TR to preserve a steady state of magnetization in the VOI associated with the imaging pulse sequence;
   d) performing, with the MRI system, the integrated pulse sequence by:
      i) performing the imaging pulse sequence to acquire imaging data from the VOI;
      ii) performing the navigator pulse sequence to acquire navigator data VOI;
      iii) processing the navigator data to generate motion estimates of motion in the VOI;
      iv) creating an updated imaging pulse sequence that prospectively corrects for the motion in the VOI using the motion estimates;
      v) repeating steps i) through iv) using the updated imaging pulse sequence; and
   e) reconstructing the imaging data to form at least one three-dimensional image of the VOI.

2. The method of claim 1 wherein the volume navigator pulse sequence includes a vNavs pulse sequence.

3. The method of claim 1 wherein the imaging pulse sequence includes a gradient echo pulse sequence.

4. The method of claim 1 wherein the integrated pulse sequence includes the EPI technique and a gradient echo technique.

5. The method of claim 1 wherein the navigator TR is matched with the imaging TR.

6. The method of claim 1 wherein the VOI includes a head of a subject and the volume navigator pulse sequence is configured to acquire navigator data from the head.

7. A magnetic resonance imaging (MRI) system, comprising:

a magnet system configured to generate a static magnetic field about at least a volume of interest (VOI) of a subject arranged in the MRI system;

a gradient coil system configured to establish at least one magnetic gradient field with respect to the static magnetic field;

a radio frequency (RF) system configured to deliver excitation pulses to the subject and acquire data from the subject;

a computer system programmed to:
  receive an indication of an imaging pulse sequence that utilizes gradient fields to generate transverse magnetization to acquire imaging data from the VOI during an imaging repetition time (TR);
  receive an indication of a volume navigator pulse sequence that uses an echo-planar imaging (EPI) technique to acquire navigator data from the VOI during a navigator TR;
  create an integrated pulse sequence that integrates the volume navigator pulse sequence with the imaging pulse sequence by coordinating the navigator TR with the imaging TR to preserve a steady state of magnetization in the VOI associated with the imaging pulse sequence;
  control the gradient coil system and the RF system to perform the integrated pulse sequence by:
    i) performing the imaging pulse sequence to acquire imaging data from the VOI;
    ii) performing the navigator pulse sequence to acquire navigator data VOI;
    iii) processing the navigator data to generate motion estimates of motion in the VOI;
    iv) creating an updated imaging pulse sequence that prospectively corrects for the motion in the VOI using the motion estimates;
    v) repeating steps i) through iv) using the updated imaging pulse sequence; and
  reconstruct the imaging data to form at least one three-dimensional image of the VOI.

8. The system of claim 7 wherein the volume navigator pulse sequence includes a vNavs pulse sequence.

9. The system of claim 7 wherein the imaging pulse sequence includes a gradient echo pulse sequence.

10. The system of claim 7 wherein the integrated pulse sequence includes the EPI technique and a gradient echo technique.

11. The system of claim 7 wherein the navigator TR is matched with a TR of the imaging pulse sequence.

12. The system of claim 7 wherein the VOI includes a head of a subject and the volume navigator pulse sequence is configured to acquire navigator data from the head.

13. A method for directing a magnetic resonance imaging (MRI) system to form echo signals from spins in a volume-of-interest (VOI), the steps of the method comprising:
  a) selecting an imaging pulse sequence that utilizes gradient fields to generate transverse magnetization to acquire imaging data from the VOI during an imaging repetition time (TR);
  b) selecting a volume navigator pulse sequence that uses an echo-planar imaging (EPI) technique to acquire navigator data from the VOI during a navigator TR;
  c) creating an integrated pulse sequence that uses a common radio frequency (RF) pulse for the volume navigator pulse sequence and the imaging pulse sequence to preserve a steady state of magnetization in the VOI;
  d) performing, with the MRI system, the integrated pulse sequence by:
    i) performing the imaging pulse sequence to acquire imaging data from the VOI;
    ii) performing the navigator pulse sequence to acquire navigator data VOI;
    iii) processing the navigator data to generate motion estimates of motion in the VOI;
    iv) creating an updated imaging pulse sequence that prospectively corrects for the motion in the VOI using the motion estimates;
    v) repeating steps i) through iv) using the updated imaging pulse sequence; and
  e) reconstructing the imaging data to form at least one three-dimensional image of the VOI.

14. The method of claim 13 wherein the volume navigator pulse sequence includes a vNavs pulse sequence.

15. The method of claim 13 wherein the imaging pulse sequence includes a gradient echo pulse sequence.

16. The method of claim 13 wherein the integrated pulse sequence includes the EPI technique and a gradient echo technique.

17. The method of claim 13 wherein the navigator TR is matched with the imaging TR.

18. The method of claim 13 wherein the VOI includes a head of a subject and the volume navigator pulse sequence is configured to acquire navigator data from the head.

* * * * *